United States Patent [19]

Penney

[11] Patent Number: 5,212,505
[45] Date of Patent: May 18, 1993

[54] ALIGNMENT SYSTEM FOR KERATOGRAPH

[75] Inventor: Carl M. Penney, Saratoga Springs, N.Y.

[73] Assignee: General Electric Company, Schenectady, N.Y.

[21] Appl. No.: 807,547

[22] Filed: Dec. 16, 1991

[51] Int. Cl.⁵ .......................... A61B 3/14; A61B 3/10
[52] U.S. Cl. .................................. 351/208; 351/212; 351/247
[58] Field of Search ...................... 351/208, 212, 247; 356/376; 128/745; 354/62

[56] References Cited

U.S. PATENT DOCUMENTS 4,750,489 6/1988 Berkman .
4,812,033 3/1989 Ishikawa ........................ 351/208

Primary Examiner—Rodney B. Bovernick
Attorney, Agent, or Firm—Patrick R. Scalon; Paul R. Webb, II

[57] ABSTRACT

An alignment system for use with a keratoscope to form an eye measurement system uses a source of a light beam which is directed towards a cornea. A reflection from that beam is supplied to first and second quadrant detectors which are connected to circuits to generate an output when the cornea is properly aligned. Upon proper alignment, the system triggers the calculation of the cornea shape by the keratoscope.

15 Claims, 2 Drawing Sheets

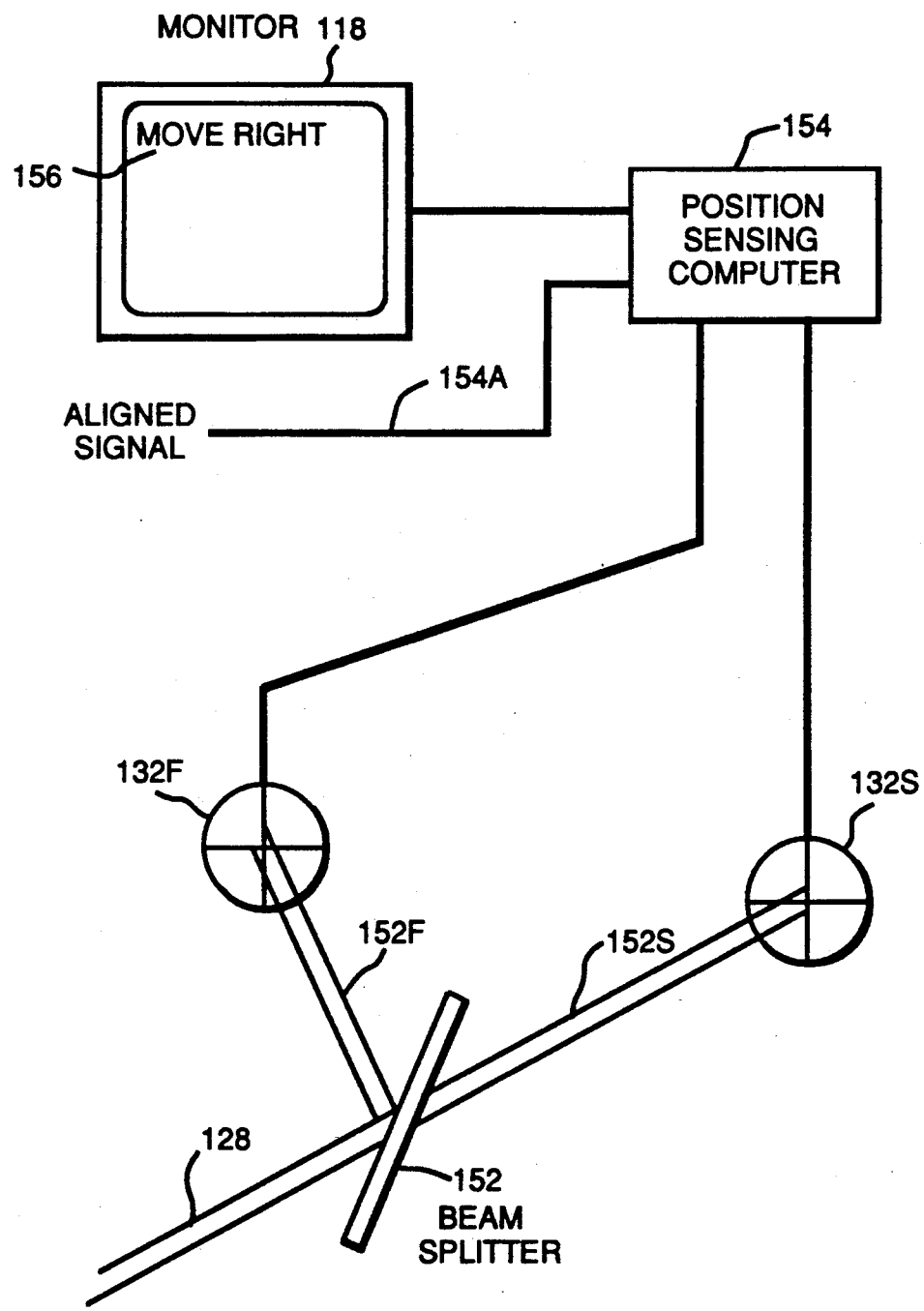

ALIGNMENT SYSTEM FOR KERATOGRAPH

CROSS REFERENCE TO RELATED APPLICATION

This application relates to copending application Ser. No. 557,263, filed Jul. 24, 1990, by Penney et al., assigned to the same assignee as the present invention.

BACKGROUND OF THE INVENTION

This invention relates to an eye measurement system. More specifically, it relates to a system for aligning the eye of a subject for keratographic (cornea shape) measurements.

There are a number of situations where the alignment of a subject's eye is important. Various known keratographs are used to determine the cornea shape of a subject's eye. However, in order to compare the cornea shape at two different times, such as before treatment and after treatment, one must be certain that the subject's eye is aligned consistently. In other words, if one measures the cornea shape when the subject is looking to the right of an instrument axis, this measured shape will be significantly different than the shape measured if the subject's eye is looking to the left of an instrument axis.

Complete alignment information relative to an eye requires x, y and z position coordinates of a point on the eye together with three angles of the eye. The three angles may, for suitable subjects, be made consistent between two different measurements by insuring that the subject is looking in a particular direction and has his or her head upright. However, accurate cornea measurement also requires that the x, y, and z coordinates of the eye are consistent.

OBJECTS AND SUMMARY OF THE INVENTION

Accordingly, a primary object of the present invention is to provide an eye measurement system for alignment of a keratograph. As used herein, "eye measurement" shall include measurement of the alignment and/or cornea shape of an eye.

A further object of the present invention is to provide a combined alignment and keratoscope system to allow the consistent measurement of a cornea.

A more specific object of the present invention is to provide an alignment system which will relatively simply and inexpensively interface to a keratoscope in order to insure that the position of a subject's eye is proper at the moment when a measurement is taken.

A still further object of the present invention is to provide an alignment system which is sufficiently accurate to produce consistent measurements within the intrinsic accuracy of the keratograph.

The above and other objects of the present invention are realized by an alignment system. The operation of said system will become more apparent as the following detailed description is considered in conjunction with the accompanying drawings.

Said alignment system contains light source for applying a light beam to a cornea of an eye. A first detector receives a portion of a reflected beam from the light beam reflecting off the cornea and a second detector, spaced from the first detector, receives the second portion of the reflected beam. An alignment means is electrically connected to the first and second detectors for generating an output that indicates when the cornea is aligned such that the reflected beam extends from the cornea along a predetermined line. The predetermined line corresponds to a reflection of the alignment beam from the cornea having a tangent plane which is normal to the instrument axis, said point lying on the instrument axis. Each of the first and second detectors may have at least three electrodes and produce a current distribution on its three electrodes which is dependent on the position of the reflected beam. More specifically, the first detector can be a quadrant detector and the second detector can be a quadrant detector.

In one embodiment, the first detector has a small hole in its center to allow light of the reflected beam to pass through going towards the second detector. In an alternate embodiment, a beam splitter is used such that the first detector receives light from the reflected beam by way of reflection from the beam splitter and the second detector receives light from the reflected beam by way of transmission through the beam splitter.

The eye measurement system includes a keratoscope for measuring the shape of a cornea. The output of the alignment means is supplied to the keratoscope to cause the keratoscope to acquire cornea shape data when the cornea is aligned. The keratoscope may, more specifically, include a TV camera, a frame grabber connected to receive a signal from the camera and a processor connected to receive and process data from the frame grabber upon the alignment means generating the output corresponding to proper alignment.

The system of the present invention may alternately be described as an eye measurement system including a light source for applying a light beam to a cornea, a first detector for receiving a light beam from the light beam reflecting off the cornea, an alignment means electrically connected to first detector for generating an output when the cornea is aligned such that the reflected beams extend from the cornea along a predetermined line, and a keratoscope for measuring the shape of a cornea. The output of the alignment means is supplied to the keratoscope to cause the keratoscope to calculate cornea shaped data when the cornea is aligned.

BRIEF DESCRIPTION OF THE DRAWINGS

The above and other features of the present invention will be more readily understood when the following detailed description is considered in conjunction with the accompanying drawings wherein like characters represent like parts throughout the several views and in which:

FIG. 2 is a combined schematic and block showing an alternate arrangement for a portion of the FIG. 1 embodiment.

DETAILED DESCRIPTION

Figure 1:
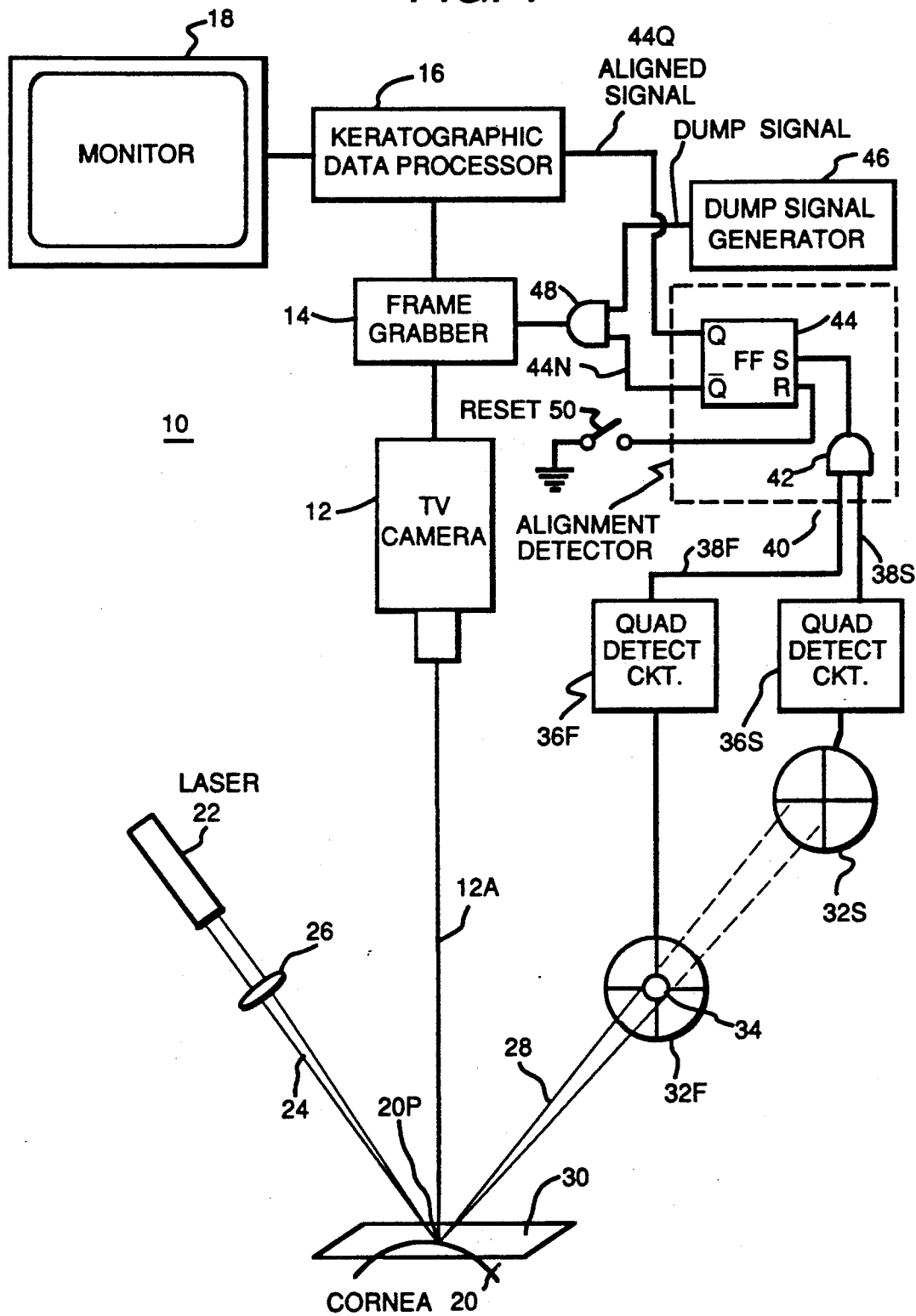
FIG. 1 is a combined schematic and block diagram of the present invention.

FIG. 1 shows a combined alignment/keratographic system 10 according to the present invention. The system 10 includes a keratoscope comprising the TV camera 12, frame grabber 14, keratographic data processor 16 and monitor 18. Components 12, 14, 16, and 18 need not be described in detail as they function in a known way, except for specific aspects discussed in more detail below, to measure the shape of the cornea 20 of the eye of a subject. Briefly, it should be noted that the frame grabber 14 stores a frame from the camera (video or other imaging type) 12 and the keratographic data processor 16 determines the shape of the cornea based upon the received information. The monitor 18 may display an image and/or data relative to the shape.

Although the components 12, 14, 16, and 18 operate in a generally conventional manner to determine the shape of the cornea 20, the present system 10 uses components hereafter discussed in order to insure that the cornea 20 is properly positioned. In order to completely define the alignment of an eye, one needs to know three angles relative to the eye as well as the position (x, y, z) of the eye. For example, the eye corresponding to cornea 20 could be looking above, below, right, or left of the instrument axis 12A corresponding to camera 12. By asking the subject to focus upon a particular object, one has determined two of the three angles (corresponding to up/down and right/left) which determine the orientation of the eye. Assume that the subject is asked to view an image which is established along the instrument axis 12A. The subject might still continue to focus on that image by turning his or her head, which movement corresponds to the third angle defining eye orientation. This third angle may therefore simply be determined by having the subject hold his or her head upright. Thus, insuring that the cornea 20 corresponds to the eye having three known or consistent angles is not very difficult when the subject cooperates. However, it may be more difficult to insure that the cornea 20 is properly aligned in terms of position, meaning that it has the proper x, y, and z coordinates. As will be discussed below, the present invention will provide for this proper positioning.

A source of light such as laser 22 supplies a light beam 24 to the cornea 20 by way of a lens 26. Because sensitive quadrant light detectors are available, a laser may be chosen that produces a sufficiently low level for eye safety. Alternately, an incoherent light source can be used. The beam 24 hits the cornea 20 and is reflected as a reflected beam 28 as if the cornea 20 was a mirror surface in tangent plane 30. The tangent plane 30 is perpendicular to the instrument axis 12A when the cornea 20 is correctly aligned. Since one knows the position of the instrument axis 12A and the position of the light beam 24, the tangent plane 30 would be readily known as a plane perpendicular to instrument axis 12A and in which the instrument axis 12A intersects with the applied light beam 24. Given the knowledge of the position of the tangent plane 30 then and the applied light beam 24, one can readily know from standard calculations where the reflected beam 28 should be disposed. In other words, proper orientation of the cornea 20 requires that the tangent plane 30 be at a point 20P for correct cornea measurement and that this tangent plane 30 be oriented perpendicular to the instrument axis 12A. Both of these conditions may be insured by applying the light beam 24 and having the axis 28 pass through at least two points, which points correspond to a predetermined line of reflection that would occur if the cornea 20 is positioned such that its point 20P along instrument axis 12A will have a tangent plane 30 perpendicular to axis 12A. Thus, in order to insure that the cornea 20 is aligned properly, one may test to determine that the reflected beam 28 lies along the predetermined line corresponding to the proper alignment.

In order to determine when the reflected beam 28 extends along the predetermined line corresponding to proper position of the cornea 20, the present system 10 uses first and second detectors 32F and 32S. As shown in the preferred embodiment of FIG. 1, the first and second detectors 32F and 32S are quadrant detectors. For illustrative purposes, the quadrant detectors are shown in perspective, but it should be appreciated that the quadrant detectors would each be oriented such that their plane would be normal to the beam 28 when beam 28 extends along the predetermined line which is indicative of proper alignment. Note that the predetermined line is not separately shown in FIG. 1 since beam 28 is illustrated as being in its proper position co-linear with that predetermined line.

The quadrant detector 32F may include a small hole in its center to allow some light to pass through to the second detector 32S. The quadrant detectors 32F and 32S may be of various known types having electrodes with a current distribution dependent upon the light which strikes the different quadrants of the detector.

Each of the respective first and second detectors 32F and 32S is connected to a corresponding quadrant detect circuit 36F and 36S. Although the connections between the detect circuits 36F and 36S and their corresponding quadrant detectors 32F and 36S are shown as a single line for ease of illustration, each quadrant detector would have at least four lines leading to the corresponding detect circuit and supplying on each line one signal corresponding to the sensed light of a corresponding quadrant. The signals provided by first detector 32F may be considered as a first plurality of signals, whereas the signals provided by second detector 32S may be considered as second plurality of signals.

The quadrant detect circuits 36F and 36S may be of various known types, such as a quadrant diode arrangement, which detect when a light beam is centered upon the particular quadrant detector. When the quadrant detect circuit 36F, by use of standard electronic circuits, detects that the reflected beam 28 is centered on first quadrant detector 32F, the circuit 36F outputs a signal on line 38F. In similar fashion, the circuit 36S outputs a signal on lie 38S when the light beam is centered on quadrant detector 32S. In order for the reflected beam 28 to be properly oriented corresponding to the proper alignment of the cornea 20, the light beam should be centered relative to both of the quadrant detectors.

The quadrant detect circuits 36F and 36S may collectively be considered as a determining means. They receive the first and second pluralities of signals respectively from the first and second detectors 32F and 32S. This determining means determines whether the reflected beam is at the intersection of the predetermined line with a first plane corresponding to first detector 32F, this determination based only on the first plurality of signals. The determining means composed of detect circuits 36F and 36S determines whether the reflected beam is at the intersection of the predetermined line with a second plane corresponding to second detector 36S, this determination being based only on the second plurality of signals. As shown in FIG. 1, each of the detectors 32F and 32S have detector elements arranged in a two-dimensional array, one detector element corresponding to each quadrant.

In order to determine when the reflected beam 28 is positioned corresponding to the cornea being properly positioned, the outputs on lines 38F and 38S are fed to an alignment detector 40. The alignment detector 40 indicates when the light beam 28 is centered in both of the quadrant detectors 32F and 32S. In the specific arrangement of FIG. 1, the alignment detector 40 may include an AND gate 42. The output of gate 42 will be logical one when the cornea 20 is properly aligned. This output from gate 42 is supplied to the S input of flip flop 44. Accordingly, when the alignment is proper, the Q output of flip flop 44 will be high, this output appearing as an aligned signal on line 44Q. This signal on line 44Q is supplied to the data processor 16. The processor 16 may simply be a microprocessor which, upon the occurrence of the aligned signal, accepts a simultaneous frame of data from the frame grabber 14 to determine the cornea shape. The alignment detector can also be configured to indicate to the subject how to move to produce alignment.

The frame grabber 14 stores a frame from the camera 12 and is constantly dumping the data within the frame grabber 14 in known fashion upon receiving a dump signal generated by the dump signal generator 46. However, the dump signal from generator 46 is supplied to the frame grabber by way of AND gate 48, whose other input is the negation of the aligned signal as appears on line 44N. Accordingly, the frame grabber 14 is constantly dumping its data after each frame and gathering new data when the cornea 20 is not properly aligned as the not Q output of flip flop 44 would be logical one. Upon the cornea 20 coming into proper alignment, the set input from gate 42 to the flip flop 44 becomes logical one such that the not Q output goes to logical zero and the Q output goes to logical one. Accordingly, the gate 48 is closed such that the dump signal no longer dumps data in the frame grabber. The generation of the aligned signal on line 44Q then causes the data processor 16 to process the data within the frame grabber. By virtue of this arrangement, the data used by the processor 16 can be obtained even if the cornea 20 is only in proper alignment momentarily.

A reset switch 50 may be used to reset the flip flop 44 when one wishes to take another measurement.

FIG. 2 shows a portion of an alternate embodiment wherein components have numbers in the 100 series with the same last two digits as the corresponding component, if any, from FIG. 1. Many of the components of the FIG. 1 embodiment would also be used in the FIG. 2 embodiment and, therefore, they are not shown for ease of illustration. For example, the laser 22, lines 26, camera 12, frame grabber 14 and data processor 16 of FIG. 1 would also be used in the FIG. 2 embodiment.

The FIG. 2 embodiment is different from FIG. 1 in that the reflected beam 128 of FIG. 2 is supplied to a beam splitter 152 which reflects a first portion of 152F of beam 128 and transmits a second portion 152S of beam 128. The first and second beam portions are respectively supplied to first and second quadrant detectors 132F and 132S. Since light does not need to pass through the quadrant 132F to reach the quadrant 132S, the quadrant detector 132F does not use a hole in it such as used by the first quadrant detector 32F in FIG. 1.

If desired, the quadrant detectors 132F and 132S of FIG. 2 may be connected to quadrant detect circuits such as shown in FIG. 1. However, the illustration of FIG. 2 shows an alternate arrangement wherein the outputs of each of the quadrant detectors 132F and 132S are fed to a position sensing computer 154. The position sensing computer 154 may simply be a microprocessor which receives digitized versions of the outputs from the quadrant detectors and determines when the reflected beam 128 is properly aligned. The computer may produce an aligned signal on output 154A which is used to cause calculation of the cornea shape in similar fashion to the use of the aligned signal and its negation in the embodiment of FIG. 1. The position sensing computer 154 thus serves as an alignment means. If desired, the computer 154 and the keratographic data processor such as 16 of FIG. 1 may be a single computer. In other words, both the position sensing functions and the cornea measurement functions may be carried out by the same microprocessor.

The position sensing computer 154 may, with appropriate software, be used to generate indicia such as 156 on the monitor 118 (which would also include unshown connections like the connections shown in FIG. 1 for monitor 18) to indicate the relative positioning between the cornea 20 and the system 10. For example, the illustrated indicia 156 says "MOVE RIGHT" in order to indicate a specific direction of relative movement required between the cornea 20 and the instrument axis 12A. Use of such indicia may make it easier to line up the cornea 20 (not shown in FIG. 2) in the proper position corresponding to the reflected beam 128 extending along a predetermined line.

Although the position sensing computer 154 has been shown used with the beam splitter arrangement of FIG. 2, the position sensing computer 154 could alternately be used with a pair of quadrant detectors such as in the embodiment of FIG. 1.

Although various specific arrangements have been shown and described herein, it is to be understood that these are for illustrative purposes only. Various modifications and adaptations will be readily apparent to those of skill in the art. Although this invention has been described with reference to alignment of a keratograph, it should be understood that the same invention can be applied to other devices requiring alignment. Accordingly, the scope of the present invention should be determined by reference to the claims appended hereto.

What is claimed is:

1. A system for eye measurement comprising:
    a light source for applying a light beam to a cornea of an eye;
    a first detector for receiving a reflected beam from the light beam reflecting off the cornea;
    a second detector, spaced from said first detector, for receiving the reflected beam; and
    alignment means electrically connected to said first detector and said second detector for generating an aligned signal only when the cornea is aligned such that said reflected beam extends from the corneas long a predetermined line; and
    wherein said first detector provides a first plurality of signals and said second detector provides a second plurality of signals, each of said first and second detectors has detector elements in a two-dimensional array, each of said first and second detectors is disposed to detect the position of said reflected beam at respective first and second planes which are intersected by said predetermined line; and further comprising
    determining means receiving said first and second pluralities of signals for determining whether said reflected beam is at the intersection of said predetermined line with said first plane based only on said first plurality of signals and for determining whether said reflected beam is at the intersection of said predetermined line with said second plane based only on said second plurality of signals, said determining means providing outputs to said alignment means.

2. The system of claim 1 wherein said predetermined line corresponds tot he cornea having a tangent plane which is normal to an instrument axis, the tangent plane having a point of intersection of said instrument axis and said light beam.

3. The system of claim 1 wherein said first detector has at least three electrodes and produces a current distribution on said three electrodes dependent on the position of the reflected beam, and said second detector has at least three electrodes an produces a current distribution on said three electrodes dependent on the position of the reflected beam.

4. The system of claim 1 wherein said first detector is a quadrant detector, and said second detector is a quadrant detector.

5. The system of claim 1 wherein said first detector has a small hole in its center to allow light of said reflected beam to pass through going towards said second detector.

6. The system of claim 1 further comprising a beam splitter, and wherein said first detector receives light from said reflected beam by way of reflection from said beam splitter and said second detector receives light from said reflected beam by way of transmission through said beam splitter.

7. A system for eye measurement comprising:
a light source for applying a light beam to a cornea of an eye;
a first detector for receiving a reflected beam from the light beam reflecting off the cornea;
a second detector, spaced from said first detector, for receiving the reflected beam; and
alignment means electrically connected to said first detector and said second detector for generating an output when the cornea is aligned such that said reflected beam extend from the cornea along a predetermined line and wherein said first detector is a quadrant detector, and said second detector is a quadrant detector and wherein said first detector has a small hole in its center to allow light of said reflected beam to pass through going towards said second detector.

8. A system for eye measurement comprising:
a light source for applying a light beam to a cornea of an eye;
a first detector for receiving a reflected beam from the light beam reflecting off the cornea;
a second detector, spaced from said first detector, for receiving the reflected beam; and
alignment means electrically connected to said first detector and said second detector for generating an output when the cornea is aligned such that said reflected beam extend from the cornea along a predetermined line and wherein said first detector is a quadrant detector, and said second detector is a quadrant detector and further comprising a beam splitter, and when said first detector receives light form said reflected beam by way of reflection from said beam splitter and said second detector receives light from said reflected beam by way of transmission through said beam splitter.

9. A system for eye measurement comprising:
a light source for applying a light beam to a cornea of an eye;
a first detector for receiving a reflected beam from the light beam reflecting off the cornea;
a second detector, spaced from said first detector, for receiving the reflected beam; and
alignment means electrically connected to said first detector and said second detector for generating an output when the cornea is aligned such that said reflected beam extend from the cornea along a predetermined line and wherein said first detector is a quadrant detector, and said second detector is a quadrant detector and further comprising a keratoscope for measuring the shape of a cornea and wherein the output of said alignment means is supplied to said keratoscope to cause said keratoscope to calculate cornea shape data when the cornea is aligned.

10. The system of claim 5 wherein said keratoscope includes a camera, a frame grabber connected to receive a signal from the cameras, and a processor connected to receive and process data from the frame grabber upon the alignment means generating said output.

11. A system for eye measurement comprising:
a light source for applying a light beam to a cornea of an eye;
a first detector for receiving a reflected beam from the light beam reflecting off the cornea;
alignment means electrically connected to said first detector for generating an output when the cornea is aligned such that said reflected beam extends from the cornea along a predetermined line; and
a keratoscope for measuring the shape of a cornea; and wherein said output of said alignment means is supplied to said keratoscope to cause said keratoscope to calculate cornea shape data when the cornea is aligned and wherein said keratoscope has an instrument axis, and wherein said predetermined line corresponds to the cornea having a tangent plane which is normal to said instrument axis, the tangent plane having a point of intersection of said instrument axis and said light beam; and further comprising a second detector, spaced from said first detector, for receiving the reflected beam; and wherein said first detector is a quadrant detector, and said second detector is a quadrant detector; and wherein said first detector has a small hole in its center to allow light of said reflected beam to pass through going towards said second detector.

12. The system of claim 11 wherein said keratoscope includes a camera, a frame grabber connected to receive a signal from the camera, and a processor connected to receive and process data from the frame grabber upon the alignment means generating such output.

13. The system of claim 11 wherein said first detector has at least two electrodes and produces a current distribution on said two electrodes dependent on the position of the reflected beam.

14. A system for eye measurement comprising:
a light source for applying a light beam to a cornea of an eye ;
a first detector for receiving a reflected beam from the light beam reflecting off the cornea;
alignment means electrically connected to said first detector for generating an output when the cornea is aligned such that said reflected beam extends from the cornea along a predetermined line; and
a keratoscope for measuring the shape of a cornea; and wherein said output of said alignment means is supplied to said keratoscope to cause said keratoscope to calculate cornea shape data when the cornea is aligned and wherein said keratoscope has an instrument axis, and wherein said predetermined line corresponds to the cornea having a tangent plane which is normal to said instrument axis, the tangent plane having a point of intersection of said instrument axis and said light beam; and further comprising a second detector, spaced from said first detector, for receiving the reflected beam; and wherein said first detector is a quadrant detector, and said second detector is a quadrant detector; and further comprising a beam splitter, and wherein said first detector receives light from said reflected beam by way of reflection from said beam splitter and said second detector receives light from said reflected beam by way of transmission through said beam splitter.

15. The system of claim 14 wherein said keratoscope includes a camera, a frame grabber connected to receive a signal from the camera, and a processor connected to receive and process data from the frame grabber upon the alignment means generating such output.

* * * * *